(12) United States Patent
Sadri et al.

(10) Patent No.: US 9,784,664 B2
(45) Date of Patent: Oct. 10, 2017

(54) MULTIDIMENSIONAL HYDRODYNAMIC FOCUSING CHAMBER

(71) Applicant: Bio-Rad Laboratories, Inc., Hercules, CA (US)

(72) Inventors: Amir M. Sadri, Toronto (CA); Tal Rosenzweig, Toronto (CA); Nenad Kircanski, Toronto (CA)

(73) Assignee: Bio-Rad Laboratories, Inc., Hercules, CA (US)

( * ) Notice: Subject to any disclaimer, the term of this patent is extended or adjusted under 35 U.S.C. 154(b) by 179 days.

(21) Appl. No.: 14/479,155

(22) Filed: Sep. 5, 2014

(65) Prior Publication Data

US 2015/0064694 A1 Mar. 5, 2015

Related U.S. Application Data

(60) Provisional application No. 61/874,320, filed on Sep. 5, 2013, provisional application No. 61/902,664, filed on Nov. 11, 2013.

(51) Int. Cl.
*G01N 1/10* (2006.01)
*G01N 15/14* (2006.01)
(Continued)

(52) U.S. Cl.
CPC ........ *G01N 15/1459* (2013.01); *B01L 3/0265* (2013.01); *B01L 3/502761* (2013.01); *B01L 3/502776* (2013.01); *C12Q 1/24* (2013.01); *G01N 15/1404* (2013.01); *B01L 2200/027* (2013.01); *B01L 2200/0652* (2013.01); *B01L 2200/0689* (2013.01); *B01L 2200/12* (2013.01); *B01L 2200/146* (2013.01); *B01L 2200/147* (2013.01); *B01L 2200/16* (2013.01); *B01L 2300/021* (2013.01); *B01L 2300/044* (2013.01); *B01L 2300/0636* (2013.01); *B01L 2300/088* (2013.01); *B01L 2300/0816* (2013.01); *B01L 2300/0864* (2013.01);
(Continued)

(58) Field of Classification Search
None
See application file for complete search history.

(56) References Cited

U.S. PATENT DOCUMENTS 4,743,361 A 5/1988 Schram
4,756,427 A 7/1988 Göhde et al.
(Continued)

FOREIGN PATENT DOCUMENTS

| CN | 101253401 A | 8/2008 |
|---|---|---|
| EP | 2153898 A1 | 2/2010 |
| WO | 2010144814 A2 | 12/2010 |

OTHER PUBLICATIONS

William H.Grover, et al., "Monolithic membrane valves and diaphragm pumps for practical large-scale integration into glass microfluidic devices", Science Direct, Sensors and Actuators B, vol. 89, 2003, pp. 315-323.
(Continued)

*Primary Examiner* — Robert Xu
(74) *Attorney, Agent, or Firm* — Kolisch Hartwell, P.C.

(57) ABSTRACT

Systems, including apparatus and methods, for the microfluidic manipulation, dispensing, and/or sorting of particles, such as cells and/or beads. The systems may include a shaped focusing chamber and/or a branched diverting mechanism.

16 Claims, 8 Drawing Sheets

(51) Int. Cl.
*B01L 3/00* (2006.01)
*B01L 3/02* (2006.01)
*C12Q 1/24* (2006.01)

(52) U.S. Cl.
CPC ..... *B01L 2300/165* (2013.01); *B01L 2300/18* (2013.01); *B01L 2400/0409* (2013.01); *B01L 2400/0415* (2013.01); *B01L 2400/0457* (2013.01); *B01L 2400/065* (2013.01); *B01L 2400/0644* (2013.01); *B01L 2400/0655* (2013.01); *B01L 2400/0688* (2013.01); *B01L 2400/082* (2013.01); *B01L 2400/084* (2013.01); *G01N 2015/149* (2013.01); *G01N 2015/1413* (2013.01); *Y10T 436/25* (2015.01); *Y10T 436/25375* (2015.01)

(56) References Cited

U.S. PATENT DOCUMENTS

| | | | |
|---|---|---|---|
| 5,808,737 | A * | 9/1998 | Edens ................ G01N 15/1404 356/246 |
| 5,837,200 | A | 11/1998 | Diessel et al. |
| 6,540,895 | B1 | 4/2003 | Spence et al. |
| 6,657,713 | B2 | 12/2003 | Hansen |
| 6,877,528 | B2 | 4/2005 | Gilbert et al. |
| 7,258,774 | B2 | 8/2007 | Chou et al. |
| 7,311,476 | B2 * | 12/2007 | Gilbert .................. B65G 51/08 406/195 |
| 7,389,879 | B2 | 6/2008 | Tyvoll et al. |
| 7,758,811 | B2 | 7/2010 | Durack et al. |
| 7,760,351 | B2 | 7/2010 | Cox et al. |
| 8,004,661 | B2 | 8/2011 | Luscher |
| 8,871,500 | B2 | 10/2014 | Foster et al. |
| 9,109,197 | B2 | 8/2015 | Yasuda et al. |
| 2003/0027225 | A1 | 2/2003 | Wada et al. |
| 2003/0054558 | A1 | 3/2003 | Kurabayashi et al. |
| 2007/0009386 | A1 | 1/2007 | Padmanabhan et al. |
| 2008/0213821 | A1 | 9/2008 | Liu et al. |
| 2010/0303687 | A1 | 12/2010 | Blaga et al. |
| 2011/0045993 | A1 | 2/2011 | Kent et al. |
| 2012/0009025 | A1 | 1/2012 | Gilbert et al. |
| 2012/0181460 | A1 | 7/2012 | Eberhart et al. |

OTHER PUBLICATIONS

William H. Grover, et al., "Teflon films for chemically-inert microfluidic valves and pumps", Lab on a Chip, vol. 8, Apr. 11, 2008, pp. 913-918.
Blaine R. Copenheaver, Authorized Officer, U.S. Patent and Trademark Office, "International Search Report" in connection with related PCT Patent App. No. PCT/US2014/054408, dated Dec. 22, 2014, 3 pages.
Blaine R. Copenheaver, Authorized Officer, U.S. Patent and Trademark Office, "Written Opinion of the International Searching Authority" in connection with related PCT Patent App. No. PCT/US2014/054408, dated Dec. 22, 2014, 7 pages.
Godin, Jessica et al., "Microfluidics and photonics for Bio-System-on-a-Chip: A review of advancements in technology towards a microfluidic flow cytometry chip", Journal of Biophotonics, vol. 1, No. 5, Oct. 2008, pp. 355-376.
Klank, H. et al., "PIV measurements in a microfluidic 3D-sheathing structure with three-dimensional flow behaviour", Journal of Micromechanics and Microengineering, vol. 12, Oct. 3, 2002, pp. 862-869.
European Patent Office, "Partial Supplementary European Search Report" in connection with related European Patent Application No. 14842644.8, dated Apr. 10, 2017, 9 pages.
Wolff, A. et al., "Integrating advanced functionality in a microfabricated high-throughput fluorescent-activated cell sorter", Lab on a Chip, vol. 3, Jan. 23, 2003, pp. 22-27.
European Patent Office, "Extended European Search Report" in connection with elated European Patent Application No. 14841752.0, dated Mar. 6, 2017, 7 pages.
European Patent Office, "Extended Search Report" in connection with related European atent Application No. 14842644.8, dated Jul. 21, 2017, 16 pages.

* cited by examiner

MULTIDIMENSIONAL HYDRODYNAMIC FOCUSING CHAMBER

CROSS-REFERENCES

This application is based upon and claims the benefit under 35 U.S.C. §119(e) of the following U.S. provisional patent applications: Ser. No. 61/874,320, filed Sep. 5, 2013; and Ser. No. 61/902,664, filed Nov. 11, 2013. Each of these applications is incorporated herein by reference in its entirety for all purposes.

INTRODUCTION

The ability to perform molecular and cellular analyses of biological systems has grown explosively over the past several decades. In particular, the advent and refinement of molecular and cellular techniques, such as DNA sequencing, gene cloning, monoclonal antibody production, cell transfection, amplification techniques (such as PCR), and transgenic animal formation, have fueled this explosive growth. These techniques have spawned an overwhelming number of identified genes, encoded proteins, engineered cell types, and assays for studying these genes, proteins, and cell types. Unfortunately, as the number of possible combinations of samples, reagents, and assays becomes nearly incalculable, it has become increasingly apparent that novel approaches are necessary even to begin to make sense of this complexity, especially within reasonable temporal and monetary limitations.

One approach to these difficulties has been to reduce the scale of assays, focusing on small volumes and small numbers of particles, including individual cells. The traditional method for dispensing a single cell (or other particle) for analysis is through dilution. Specifically, a solution containing the cells is diluted to a concentration such that each absorption/dispensing of pipette contains on average a single cell. However, this method is not accurate: aliquots may contain no cell, one cell, or multiple cells. Single cells also may be dispensed by pick-and-place robot systems, which locate an individual cell (for example, on a dish), pick up the cell, and place the cell at another location. However, pick-and-place systems need to locate each cell and require significant time if moving a substantial number of cells. Single cells also may be analyzed using flow cytometry, but this method is complex and expensive, and not set up for or intended to dispense single cells.

Thus, in view of these shortcomings, there is a need for systems that can effectively manipulate individual cells and other small particles, such as beads, in small volumes.

SUMMARY

The invention provides systems, including apparatus and methods, for the microfluidic manipulation, dispensing, and/or sorting of particles, such as cells and/or beads. The systems may include a shaped focusing chamber (e.g., a four-sided chamber) and/or a branched diverting mechanism.

DETAILED DESCRIPTION

Figure 1:
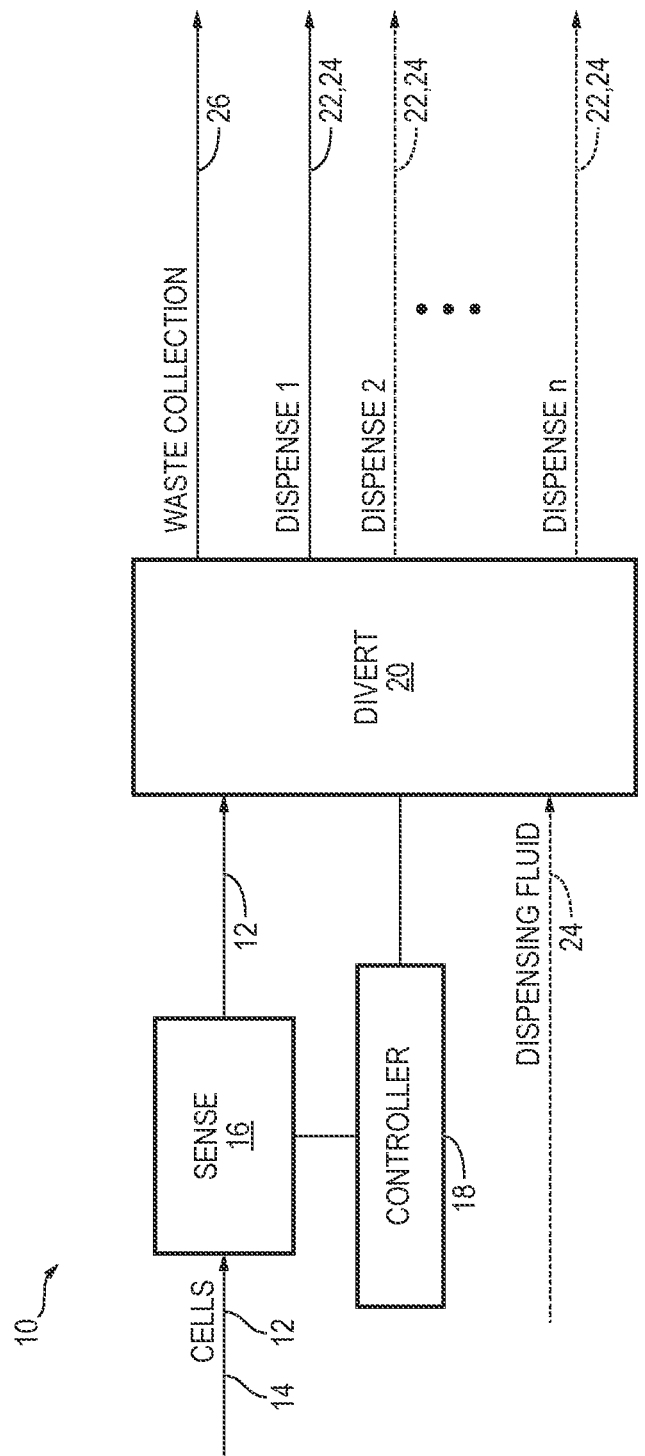
FIG. 1 is a schematic diagram showing an illustrative on-demand cell dispensing system according to aspects of the present disclosure.
Figure 2:
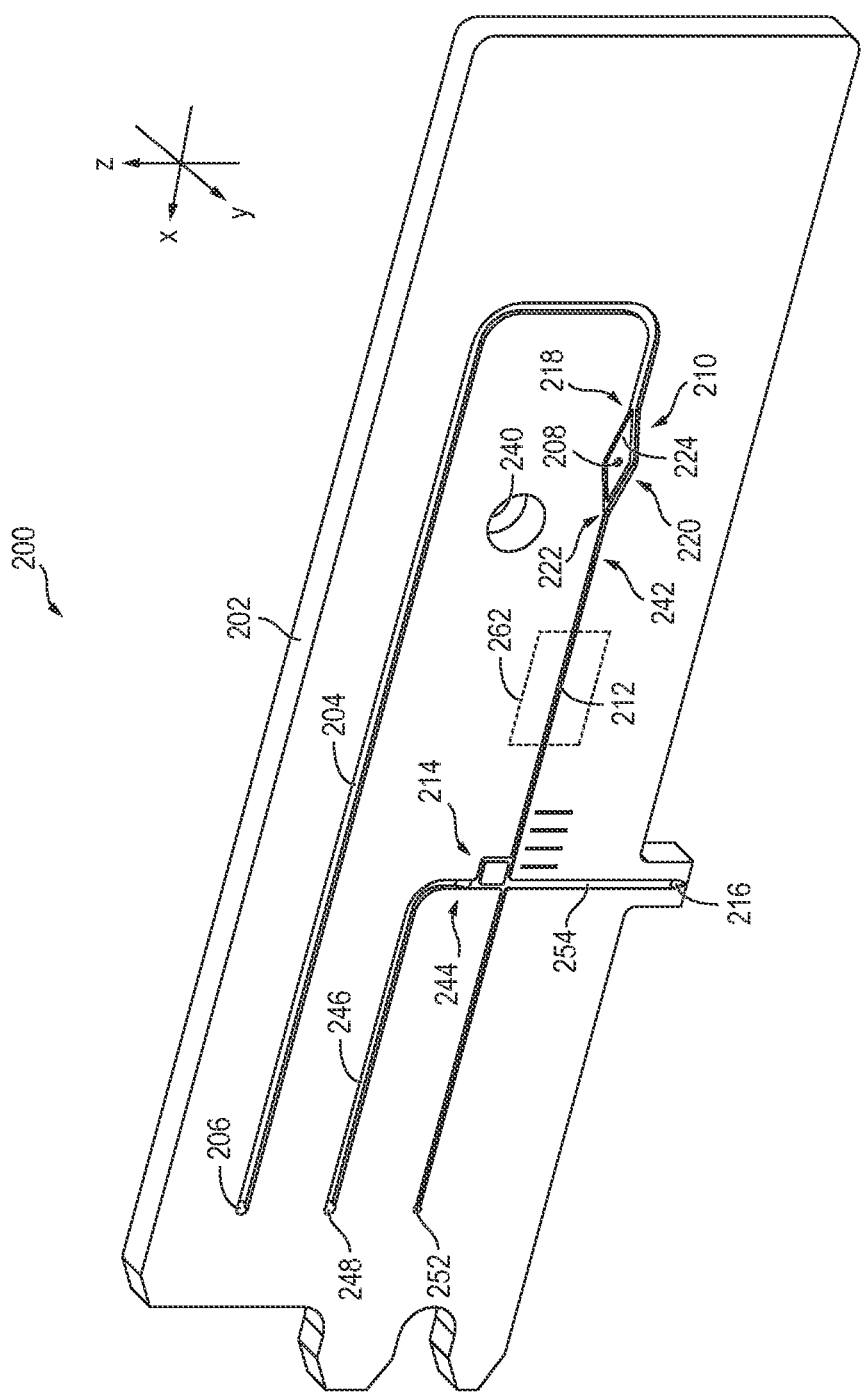
FIG. 2 is an isometric view of an illustrative microfluidic chip including a focusing chamber and an on-demand dispensing mechanism in accordance with aspects of the present disclosure.
Figure 3:
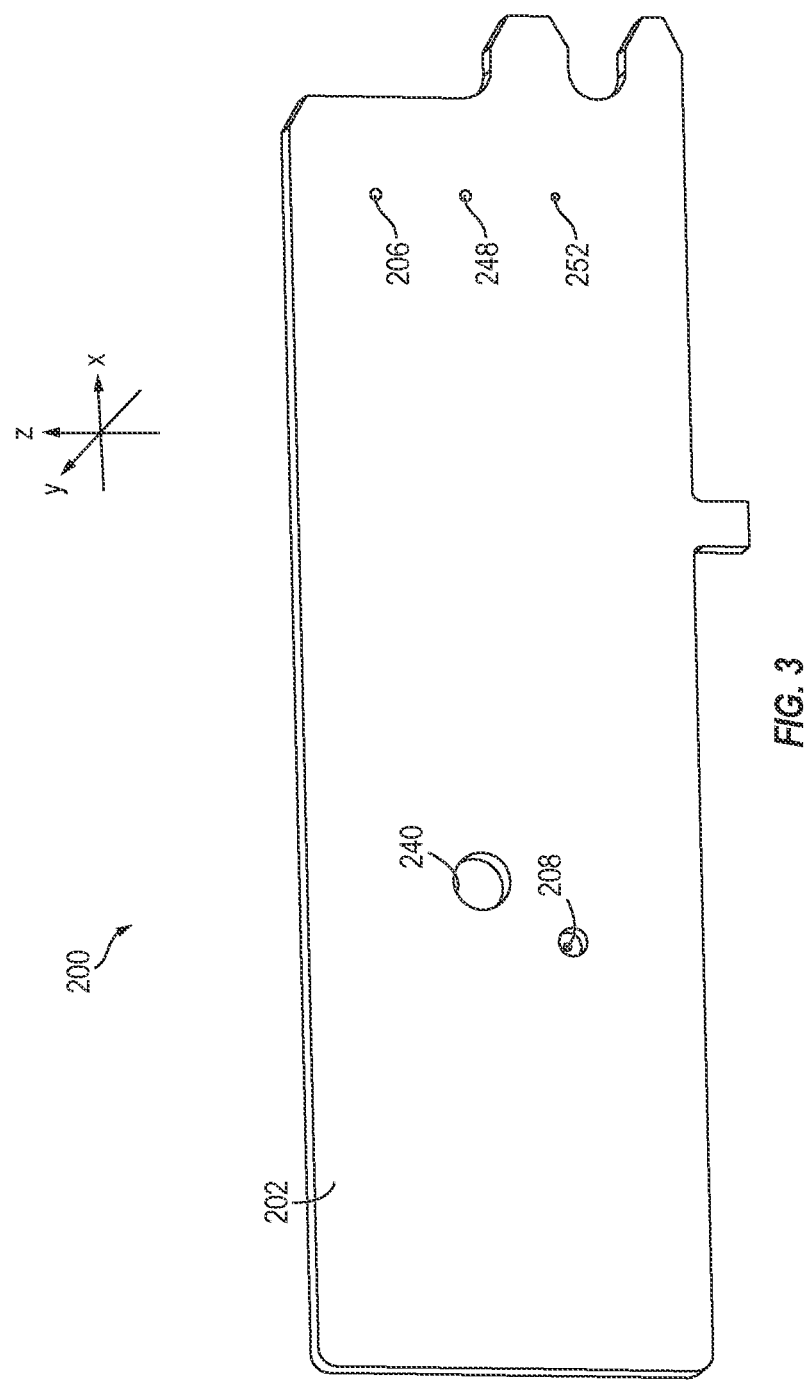
FIG. 3 is an isometric view of the chip of FIG. 2, taken from an opposing viewpoint.
Figure 4:
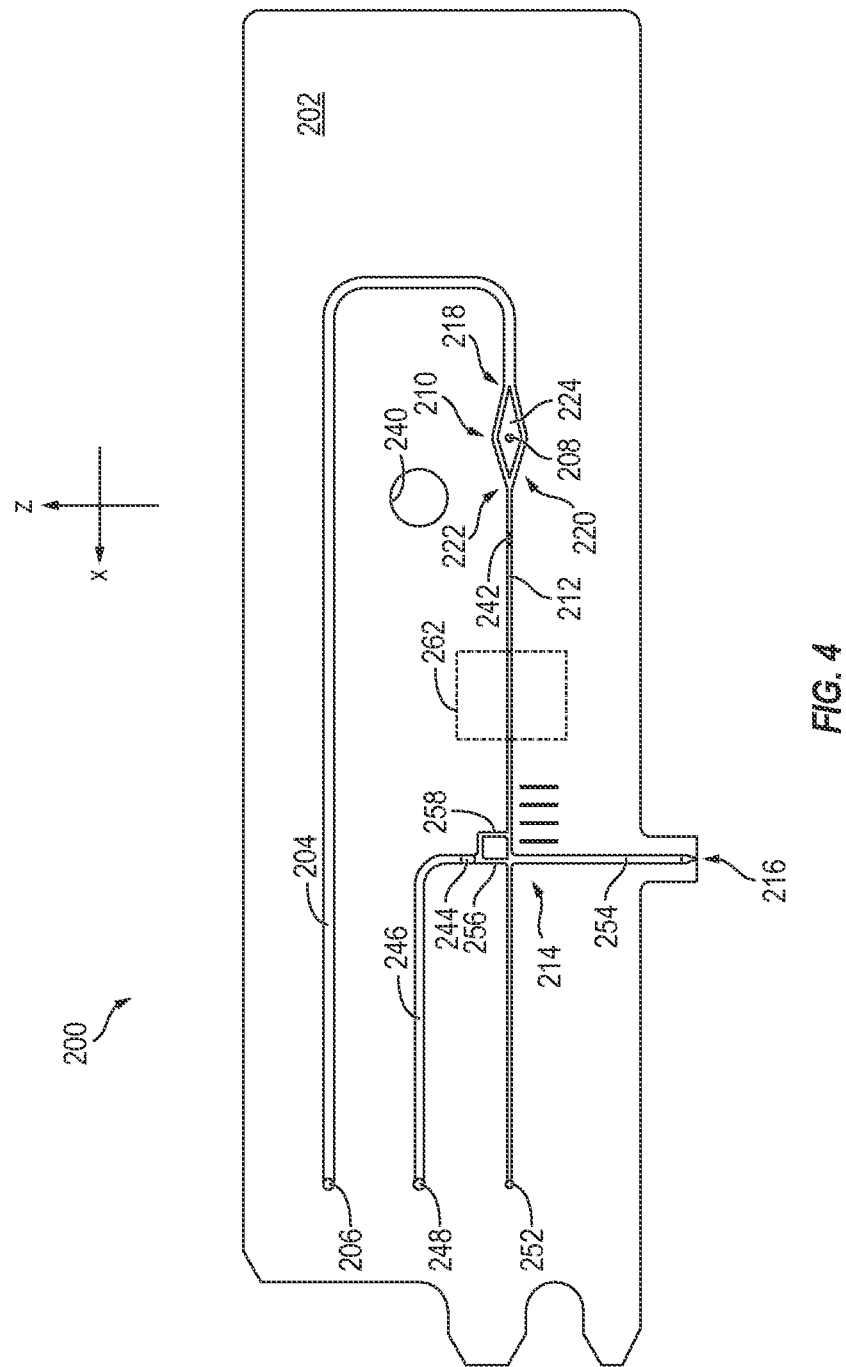
FIG. 4 is a plan view of the chip of FIG. 2, showing a microfluidic network.
Figure 5:
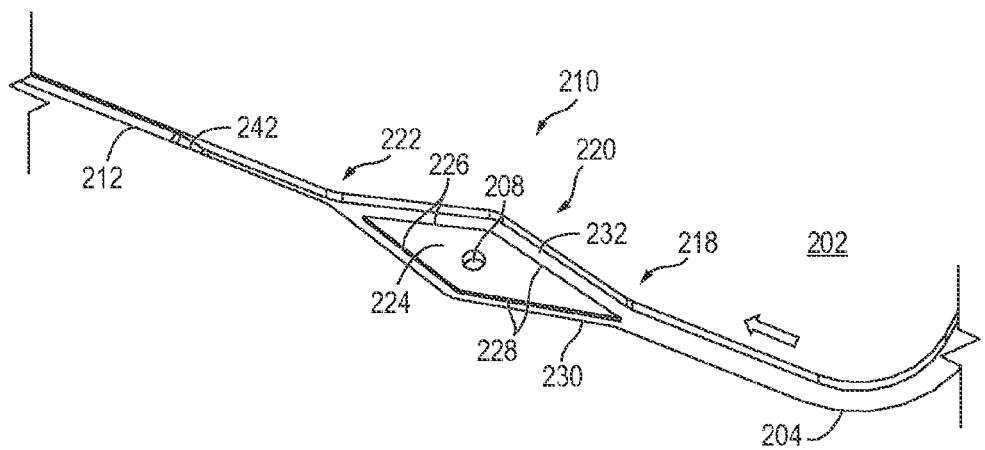
FIG. 5 is a partial isometric view of the chip of FIG. 2, showing an illustrative focusing chamber in accordance with aspects of the present disclosure.
Figure 6:
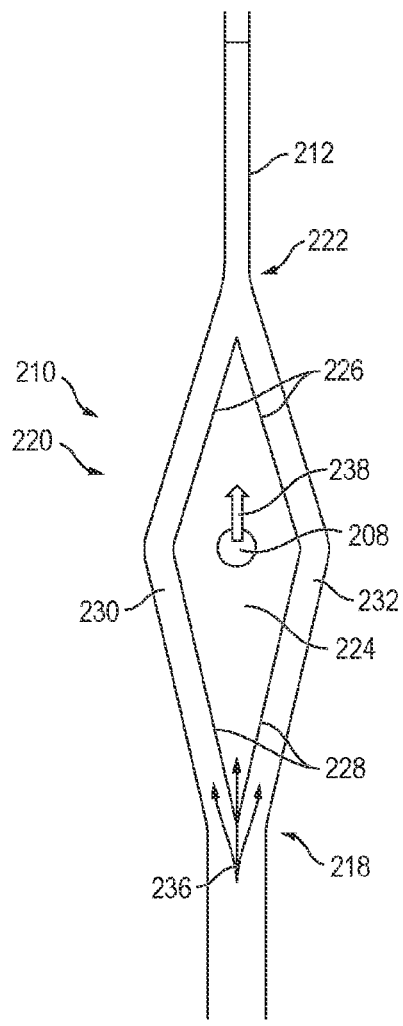
FIG. 6 is a plan view of the focusing chamber of FIG. 5.
Figure 7:
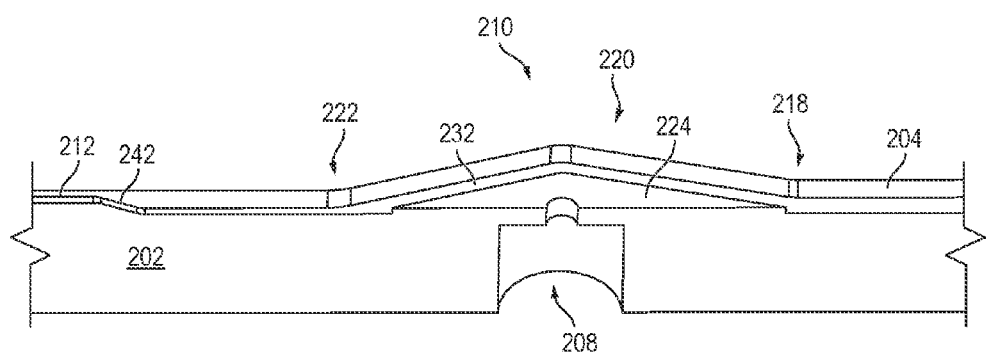
FIG. 7 is an isometric sectional view of the focusing chamber of FIG. 5.
Figure 8:
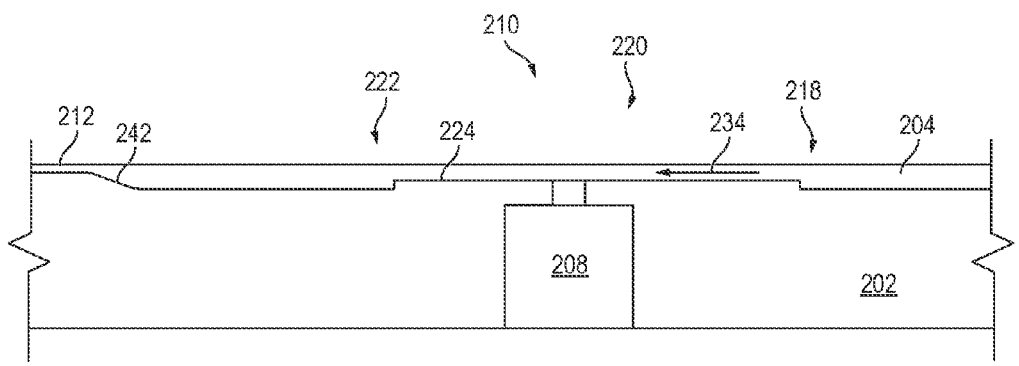
FIG. 8 is a sectional side elevation view of the focusing chamber of FIG. 5.

The invention provides systems, including apparatus and methods, for the microfluidic on-demand dispensing and/or sortation of particles, such as cells, viruses, organelles, beads, and/or vesicles. The systems may include a diamond-shaped focusing chamber and/or a branched diverting mechanism. The invention also provides microfluidic mechanisms for carrying out the dispensing and sortation. These mechanisms may enable controlled input, movement/positioning, diversion, release, and/or output of particles. Furthermore, these mechanisms may be combined in any suitable order and/or employed for any suitable number of times within a system. Accordingly, these combinations may allow particles to be sorted or dispensed, among others, as single particles, mixed groups of particles, arrays of particles, heterogeneous particle sets, and/or homogeneous particle sets, among others, in series and/or in parallel. In addition, these combinations may enable microfluidic systems to be reused. Furthermore, these combinations may allow the dispensing of particles more efficiently, reliably, precisely, and/or with more viability than was previously possible.

Further aspects of the invention are described in the following sections: (I) overview of microfluidic systems, (II) physical structures of fluid networks, (III) particles, (IV) input mechanisms, (V) measurement and detection mechanisms, (VI) output mechanisms, (VII) overview of an on-demand dispensing system, and (VIII) examples.

I. OVERVIEW OF MICROFLUIDIC SYSTEMS

A. Definitions and Overview

Particle manipulations may be performed in microfluidic systems such as those described in this disclosure. A microfluidic system generally comprises any system in which very small volumes of fluid are stored and manipulated, generally less than about 500 µL, typically less than about 100 µL, and more typically less than about 10 µL. Microfluidic systems carry fluid in predefined paths through one or more microfluidic passages. A microfluidic passage may have a minimum dimension, generally height or width, of less than about 200, 100, or 50 µm. Passages are described in more detail below in Section II.

Microfluidic systems may include one or more sets of passages that interconnect to form a generally closed microfluidic network. Such a microfluidic network may include one, two, or more openings at network termini, or intermediate to the network, that interface with the external world. Such openings may receive, store, and/or dispense fluid. Dispensing fluid may be introduced directly into the microfluidic network or to sites external the microfluidic system. Such openings generally function in input and/or output mechanisms, described in more detail below, and may include reservoirs, also described in more detail below.

Microfluidic systems also may include any other suitable features or mechanisms that contribute to fluid and/or particle manipulation. For example, microfluidic systems may include regulatory or control mechanisms that determine aspects of fluid flow rate and/or path. Valves and/or pumps that may participate in such regulatory mechanisms are described in more detail below. Alternatively or additionally, microfluidic systems may include mechanisms that determine, regulate, and/or sense fluid temperature, fluid pressure, fluid flow rate, exposure to light, exposure to electric fields, magnetic field strength, and/or the like. Accordingly, microfluidic systems may include heaters, coolers, electrodes, lenses, gratings, light sources, pressure sensors, pressure transducers, microprocessors, microelectronics, and/or so on. Furthermore, each microfluidic system may include one or more features that act as a code to identify a given system. The features may include any detectable shape or symbol, or set of shapes or symbols, such as black-and-white or colored barcode, a word, a number, and/or the like, that has a distinctive position, identity, and/or other property (such as optical property).

B. Materials

Microfluidic systems may be formed of any suitable material or combination of suitable materials. Suitable materials may include elastomers, such as polydimethylsiloxane (PDMS); plastics, such as polystyrene, polypropylene, polycarbonate, etc.; glass; ceramics; sol-gels; silicon and/or other metalloids; metals or metal oxides; biological polymers, mixtures, and/or particles, such as proteins (gelatin, polylysine, serum albumin, collagen, etc.), nucleic acids, microorganisms, etc.; and/or the like.

C. Methods of Fabrication

Microfluidic systems, also referred to as chips, may have any suitable structure. Such systems may be fabricated as a unitary structure from a single component, or as a multi-component structure of two or more components. The two or more components may have any suitable relative spatial relationship and may be attached to one another by any suitable bonding mechanism.

In some embodiments, two or more of the components may be fabricated as relatively thin layers, which may be disposed face-to-face. The relatively thin layers may have distinct thickness, based on function. For example, the thickness of some layers may be about 10 to 250 µm, 20 to 200 µm, or about 50 to 150 µm, among others. Other layers may be substantially thicker, in some cases providing mechanical strength to the system. The thicknesses of such other layers may be about 0.25 to 2 cm, 0.4 to 1.5 cm, or 0.5 to 1 cm, among others. One or more additional layers may be a substantially planar layer that functions as a substrate layer, in some cases contributing a floor portion to some or all microfluidic passages.

Components of a microfluidic system may be fabricated by any suitable mechanism, based on the desired application for the system and on materials used in fabrication. For example, one or more components may be molded, stamped, and/or embossed using a suitable mold. Such a mold may be formed of any suitable material by micromachining, etching, soft lithography, material deposition, cutting, and/or punching, among others. Alternatively, or in addition, components of a microfluidic system may be fabricated without a mold by etching, micromachining, cutting, punching, and/or material deposition.

Microfluidic components may be fabricated separately, joined, and further modified as appropriate. For example, when fabricated as distinct layers, microfluidic components may be bonded, generally face-to-face. These separate components may be surface-treated, for example, with reactive chemicals to modify surface chemistry, with particle binding agents, with reagents to facilitate analysis, and/or so on. Such surface-treatment may be localized to discrete portions of the surface or may be relatively nonlocalized. In some embodiments, separate layers may be fabricated and then punched and/or cut to produce additional structure. Such punching and/or cutting may be performed before and/or after distinct components have been joined.

II. PHYSICAL STRUCTURES OF FLUID NETWORKS

A. Overview

Microfluidic systems may include any suitable structure(s) for the integrated manipulation of small volumes of fluid, including moving and/or storing fluid, and particles associated therewith. The structures may include passages, reservoirs, and/or regulators, among others.

1. Passages or Channels

Passages generally comprise any suitable path, channel, or duct through, over, or along which materials (e.g., fluid, particles, and/or reagents) may pass in a microfluidic system. Collectively, a set of fluidically communicating passages, generally in the form of channels, may be referred to as a microfluidic network. In some cases, passages may be described as having surfaces that form a floor, a roof or ceiling, and walls. Passages may have any suitable dimensions and geometry, including width, height, length, and/or cross-sectional profile, among others, and may follow any suitable path, including linear, circular, and/or curvilinear, among others. Passages also may have any suitable surface contours, including recesses, protrusions, and/or apertures, and may have any suitable surface chemistry or permeability at any appropriate position within a channel. Suitable surface chemistry may include surface modification, by addition and/or treatment with a chemical and/or reagent, before, during, and/or after passage formation. Channels may be formed in a substrate, such as by injection molding. In some examples, this or another process may be used to create channels having a floor and walls. Such channels may be made suitable for fluidic flow by enclosing the channels. For example, channels may be enclosed by bonding or otherwise applying a sealing film or other covering to the substrate to create a ceiling or roof for the channels.

In some cases, passages, and particularly channels, may be described according to function. For example, passages may be described according to direction of material flow in a particular application, relationship to a particular reference structure, and/or type of material carried. Accordingly, passages may be inlet passages (or channels), which generally carry materials to a site, and outlet passages (or channels), which generally carry materials from a site. In addition, passages may be referred to as particle passages (or channels), reagent passages (or channels), focusing passages (or channels), perfusion passages (or channels), waste passages (or channels), and/or the like.

Passages may branch, join, and/or dead-end to form any suitable microfluidic network. Accordingly, passages may function in particle positioning, sorting, retention, treatment, detection, propagation, storage, mixing, and/or release, among others. Further aspects of passages are included throughout this Detailed Description.

2. Reservoirs

Reservoirs generally comprise any suitable receptacle or chamber for storing materials (e.g., fluid, particles and/or reagents), before, during, between, and/or after processing operations (e.g., measurement and/or treatment). Reservoirs, also referred to as wells, may include input, intermediate, and/or output reservoirs. Input reservoirs may store materials (e.g., fluid, particles, and/or reagents) prior to inputting the materials to a microfluidic network(s) portion of a chip. By contrast, intermediate reservoirs may store materials during and/or between processing operations. Finally, output reservoirs may store materials prior to outputting from the chip, for example, to an external processor or waste, or prior to disposal of the chip.

3. Regulators

Regulators generally comprise any suitable mechanism for generating and/or regulating movement of materials (e.g., fluid, particles, and/or reagents). Suitable regulators may include valves, pumps, and/or electrodes, among others. Regulators may operate by actively promoting flow and/or by restricting active or passive flow. Suitable functions mediated by regulators may include mixing, sorting, connection (or isolation) of fluidic networks, and/or the like.

III. PARTICLES

A. Overview

Microfluidic systems may be used to manipulate particles. A particle generally comprises any object that is small enough to be inputted and manipulated within a microfluidic network in association with fluid, but that is large enough to be distinguishable from the fluid. Particles, as used here, typically are microscopic or near-microscopic, and may have diameters of about 0.005 to 100 μm, 0.1 to 50 μm, or about 0.5 to 30 μm. Alternatively, or in addition, particles may have masses of about 10-20 to 10-5 grams, 10-16 to 10-7 grams, or 10-14 to 10-8 grams. Exemplary particles may include cells, viruses, organelles, beads, and/or vesicles, and aggregates thereof, such as dimers, trimers, etc.

B. Cells

1. Overview

Cells, as used here, generally comprise any self-replicating, membrane-bounded biological entity, or any nonreplicating, membrane-bounded descendant thereof. Nonreplicating descendants may be senescent cells, terminally differentiated cells, cell chimeras, serum-starved cells, infected cells, nonreplicating mutants, anucleate cells, etc.

Cells used as particles in microfluidic systems may have any suitable origin, genetic background, state of health, state of fixation, membrane permeability, pretreatment, and/or population purity, among others. Origin of cells may be eukaryotic, prokaryotic, archae, etc., and may be from animals, plants, fungi, protists, bacteria, and/or the like. Cells may be wild-type; natural, chemical, or viral mutants; engineered mutants (such as transgenics); and/or the like. In addition, cells may be growing, quiescent, senescent, transformed, and/or immortalized, among others, and cells may be fixed and/or unfixed. Living or dead, fixed or unfixed cells may have intact membranes, and/or permeabilized/disrupted membranes to allow uptake of ions, labels, dyes, ligands, etc., or to allow release of cell contents. Cells may have been pretreated before introduction into a microfluidic system by any suitable processing steps. Such processing steps may include modulator treatment, transfection (including infection, injection, particle bombardment, lipofection, coprecipitate transfection, etc.), processing with assay reagents, such as dyes or labels, and/or so on. Furthermore, cells may be a monoculture, generally derived as a clonal population from a single cell or a small set of very similar cells; may be presorted by any suitable mechanism such as affinity binding, FACS, drug selection, etc.; and/or may be a mixed or heterogeneous population of distinct cell types.

2. Eukaryotic Cells

Eukaryotic cells, that is, cells having one or more nuclei, or anucleate derivatives thereof, may be obtained from any suitable source, including primary cells, established cells, and/or patient samples. Such cells may be from any cell type or mixture of cell types, from any developmental stage, and/or from any genetic background. Furthermore, eukaryotic cells may be adherent and/or nonadherent. Such cells may be from any suitable eukaryotic organism including animals, plants, fungi, and/or protists.

Eukaryotic cells may be from animals, that is, vertebrates or invertebrates. Vertebrates may include mammals, that is, primates (such as humans, apes, monkeys, etc.) or nonprimates (such as cows, horses, sheep, pigs, dogs, cats, marsupials, rodents, and/or the like). Nonmammalian vertebrates may include birds, reptiles, fish, (such as trout, salmon, goldfish, zebrafish, etc.), and/or amphibians (such as frogs of the species *Xenopus, Rana*, etc.). Invertebrates may include arthropods (such as arachnids, insects (e.g., *Drosophila*), etc.), mollusks (such as clams, snails, etc.), annelids (such as earthworms, etc.), echinoderms (such as various starfish, among others), coelenterates (such as jellyfish, coral, etc.), porifera (sponges), platyhelminths (tapeworms), nemathelminths (flatworms), etc.

Eukaryotic cells may be from any suitable plant, such as monocotyledons, dicotyledons, gymnosperms, angiosperms, ferns, mosses, lichens, and/or *algae*, among others. Exemplary plants may include plant crops (such as rice, corn, wheat, rye, barley, potatoes, etc.), plants used in research (e.g., *Arabadopsis*, loblolly pine, etc.), plants of horticultural values (ornamental palms, roses, etc.), and/or the like.

Eukaryotic cells may be from any suitable fungi, including members of the phyla *Chytridiomycota, Zygomycota, Ascomycota, Basidiomycota, Deuteromycetes*, and/or yeasts. Exemplary fungi may include *Saccharomyces cerevisiae, Schizosaccharomyces pombe, Pichia pastoralis, Neurospora crassa*, mushrooms, puffballs, imperfect fungi, molds, and/or the like.

Eukaryotic cells may be from any suitable protists (protozoans), including amoebae, ciliates, flagellates, coccidia, microsporidia, and/or the like. Exemplary protists may include *Giardia lamblia, Entamoeba. histolytica, Cryptosporidium*, and/or *N. fowleri*, among others.

Particles may include eukaryotic cells that are primary, that is, taken directly from an organism or nature, without subsequent extended culture in vitro. For example, the cells may be obtained from a patient sample, such as whole blood, packed cells, white blood cells, urine, sputum, feces, mucus, spinal fluid, tumors, diseased tissue, bone marrow, lymph, semen, pleural fluid, a prenatal sample, an aspirate, a biopsy, disaggregated tissue, epidermal cells, keratinocytes, endothelial cells, smooth muscle cells, skeletal muscle cells, neural cells, renal cells, prostate cells, liver cells, stem cells, osteoblasts, and/or the like. Similar samples may be manipulated and analyzed from human volunteers, selected members of the human population, forensic samples, animals, plants, and/or natural sources (water, soil, air, etc.), among others.

Alternatively, or in addition, particles may include established eukaryotic cells. Such cells may be immortalized and/or transformed by any suitable treatment, including viral infection, nucleic acid transfection, chemical treatment, extended passage and selection, radiation exposure, and/or the like. Such established cells may include various lineages such as neuroblasts, neurons, fibroblasts, myoblasts, myotubes, chondroblasts, chondrocytes, osteoblasts, osteocytes, cardiocytes, smooth muscle cells, epithelial cells, keratinocytes, kidney cells, liver cells, lymphocytes, granulocytes, and/or macrophages, among others. Exemplary established cell lines may include Rat-1, NIH 3T3, HEK 293, COS1, COS7, CV-1, C2C12, MDCK, PC12, SAOS, HeLa, Schneider cells, Junkat cells, SL2, and/or the like.

3. Prokaryotic Cells

Particles may be prokaryotic cells, that is, self-replicating, membrane-bounded microorganisms that lack membrane-bound organelles, or nonreplicating descendants thereof. Prokaryotic cells may be from any phyla, including *Aquificae, Bacteroids, Chlorobia, Chrysogenetes, Cyanobacteria, Fibrobacter, Firmicutes, Flavobacteria, Fusobacteria, Proteobacteria, Sphingobacteria, Spirochaetes, Thermomicrobia*, and/or *Xenobacteria*, among others. Such bacteria may be gram-negative, gram-positive, harmful, beneficial, and/or pathogenic. Exemplary prokaryotic cells may include *E. coli, S. typhimurium, B subtilis, S. aureus, C. perfringens, V. parahaemolyticus*, and/or *B. anthracis*, among others.

C. Viruses

Viruses may be manipulated as particles in microfluidic systems. Viruses generally comprise any microscopic/submicroscopic parasites of cells (animals, plants, fungi, protists, and/or bacteria) that include a protein and/or membrane coat and that are unable to replicate without a host cell. Viruses may include DNA viruses, RNA viruses, retroviruses, virions, viroids, prions, etc. Exemplary viruses may include HIV, RSV, rabies, hepatitis virus, Epstein-Barr virus, rhinoviruses, bacteriophages, prions that cause various diseases (CJD (Creutzfeld-Jacob disease, kuru, GSS (Gerstmann-Straussler-Scheinker syndrome), FFI (Fatal Familial Insomnia), Alpers syndrome, etc.), and/or the like.

D. Organelles

Organelles may be manipulated in microfluidic systems. Organelles generally comprise any particulate component of a cell. For example, organelles may include nuclei, Golgi apparatus, lysosomes, endosomes, mitochondria, peroxisomes, endoplasmic reticulum, phagosomes, vacuoles, chloroplasts, etc.

E. Beads

Beads may be manipulated in microfluidic systems. Beads generally comprise any suitable manufactured particles. Beads may be manufactured from inorganic materials, or materials that are synthesized chemically, enzymatically and/or biologically. Furthermore, beads may have any suitable porosity and may be formed as a solid or as a gel. Suitable bead compositions may include plastics (e.g., polystyrene), dextrans, glass, ceramics, sol-gels, elastomers, silicon, metals, and/or biopolymers (proteins, nucleic acids, etc.). Beads may have any suitable particle diameter or range of diameters. Accordingly, beads may be a substantially uniform population with a narrow range of diameters, or beads may be a heterogeneous population with a broad range of diameters, or two or more distinct diameters.

Beads may be associated with any suitable materials. The materials may include compounds, polymers, complexes, mixtures, phages, viruses, and/or cells, among others. For example, the beads may be associated with a member of a specific binding pair (see Section VI), such as a receptor, a ligand, a nucleic acid, a member of a compound library, and/or so on. Beads may be a mixture of distinct beads, in some cases carrying distinct materials. The distinct beads may differ in any suitable aspect(s), such as size, shape, an associated code, and/or material carried by the beads. In some embodiments, the aspect may identify the associated material. Codes are described further below.

F. Vesicles

Particles may be vesicles. Vesicles generally comprise any noncellularly derived particle that is defined by a lipid envelope. Vesicles may include any suitable components in their envelope or interior portions. Suitable components may include compounds, polymers, complexes, mixtures, aggregates, and/or particles, among others. Exemplary components may include proteins, peptides, small compounds, drug candidates, receptors, nucleic acids, ligands, and/or the like.

IV. INPUT MECHANISMS

A. Overview

Microfluidic systems may include one or more input mechanisms that interface with the microfluidic network(s). An input mechanism generally comprises any suitable mechanism for inputting material(s) (e.g., particles, fluid, and/or reagents) to a microfluidic network of a microfluidic chip, including selective (that is, component-by-component) and/or bulk mechanisms.

B. Internal/External Sources

The input mechanism may receive material from internal sources, that is, reservoirs that are included in a microfluidic chip, and/or external sources, that is, reservoirs that are separate from, or external to, the chip.

Input mechanisms that input materials from internal sources may use any suitable receptacle to store and dispense the materials. Suitable receptacles may include a void formed in the chip. Such voids may be directly accessible from outside the chip, for example, through a hole extending from fluidic communication with a fluid network to an external surface of the chip, such as the top surface. The receptacles may have a fluid capacity that is relatively large compared to the fluid capacity of the fluid network, so that they are not quickly exhausted. For example, the fluid capacity may be at least about 1, 5, 10, 25, 50, or 100 µL. Accordingly, materials may be dispensed into the receptacles using standard laboratory equipment, if desired, such as micropipettes, syringes, and the like.

Input mechanisms that input materials from external sources also may use any suitable receptacle and mechanism to store and dispense the materials. However, if the external sources input materials directly into the fluid network, the external sources may need to interface effectively with the fluid network, for example, using contact and/or noncontact dispensing mechanisms. Accordingly, input mechanisms from external sources may use capillaries or needles to direct fluid precisely into the fluid network. Alternatively, or in addition, input mechanisms from external sources may use a noncontact dispensing mechanism, such as "spitting," which may be comparable to the action of an inkjet printer. Furthermore, input mechanisms from external sources may use ballistic propulsion of particles, for example, as mediated by a gene gun.

C. Facilitating Mechanisms

The inputting of materials into the microfluidics system may be facilitated and/or regulated using any suitable facilitating mechanism. Such facilitating mechanisms may include gravity flow, for example, when an input reservoir has greater height of fluid than an output reservoir. Facilitating mechanisms also may include positive pressure to push materials into the fluidic network, such as mechanical or gas pressure, or centrifugal force; negative pressure at an output mechanism to draw fluid toward the output mechanism; and/or a positioning mechanism acting within the fluid network. The positioning mechanism may include a pump and/or an electrokinetic mechanism.

V. MEASUREMENT AND DETECTION MECHANISMS

A. Overview

Particles manipulated by a microfluidic system may be analyzed by one or more measurement mechanisms at one or more measurement sites. The measurement mechanisms generally comprise any suitable apparatus or method for detecting a preselected particle or particle characteristic (provided, for example, by the particle, a particle component, and/or an assay product, among others). The measurement sites generally comprise any suitable particle position or positions at which a measurement is performed, internal and/or external to the system.

B. Detection Methods

The measurement mechanism may employ any suitable detection method to analyze a sample, qualitatively and/or quantitatively. Suitable detection methods may include spectroscopic methods, electrical methods, hydrodynamic methods, imaging methods, and/or biological methods, among others, especially those adapted or adaptable to the analysis of particles. These methods may involve detection of single or multiple values, time-dependent or time-independent (e.g., steady-state or endpoint) values, and/or averaged or (temporally and/or spatially) distributed values, among others. These methods may measure and/or output analog and/or digital values.

Spectroscopic methods generally may include detection of any property of light (or a wavelike particle), particularly properties that are changed via interaction with a sample. Suitable spectroscopic methods may include absorption, luminescence (including photoluminescence, chemiluminescence, and electrochemiluminescence), magnetic resonance (including nuclear and electron spin resonance), scattering (including light scattering, electron scattering, and neutron scattering), diffraction, circular dichroism, and optical rotation, among others. Suitable photoluminescence methods may include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), fluorescence activated cell sorting (FACS), and their phosphorescence and other analogs, among others.

Electrical methods generally may include detection of any electrical parameter. Suitable electrical parameters may include current, voltage, resistance, impedance, capacitance, and/or power, among others.

Hydrodynamic methods generally may include detection of interactions between a particle (or a component or derivative thereof) and its neighbors (e.g., other particles), the solvent (including any matrix), and/or the microfluidic system, among others, and may be used to characterize molecular size and/or shape, or to separate a sample into its components. Suitable hydrodynamic methods may include chromatography, sedimentation, viscometry, and electrophoresis, among others.

Imaging methods generally may include detection of spatially distributed signals, typically for visualizing a sample or its components, including optical microscopy and electron microscopy, among others.

Biological methods generally may include detection of some biological activity that is conducted, mediated, and/or influenced by the particle, typically using another method, as described above.

C. Detection Sites

The measurement mechanism may be used to detect particles and/or particle characteristics at any suitable detection site, internal and/or external to the microfluidic system.

Suitable internal detection sites may include any site(s) in or on a microfluidic system (a chip). These sites may include channels, chambers, and/or traps, and portions thereof, and may be referred to herein as sensing regions. Particles or particle characteristics may be detected while the particles (or released components/assay products) are stationary or moving. Stationary particles may be encountered following particle retention, for example, cells growing in a cell chamber. Moving particles may be encountered before and/or after particle retention, or upon confinement to a region. In particular, particles may be moved past a detection site by any suitable positioning mechanism, for example, by fluid flow (flow-based detection).

D. Detected Characteristics

The measurement method may detect and/or monitor any suitable characteristic of a particle, directly and/or indirectly (e.g., via a reporter molecule). Suitable characteristics may include particle identity, number, concentration, position (absolute or relative), composition, structure, sequence, and/or activity among others. The detected characteristics may include molecular or supramolecular characteristics, such as the presence/absence, concentration, localization, structure/modification, conformation, morphology, activity, number, and/or movement of DNA, RNA, protein, enzyme, lipid, carbohydrate, ions, metabolites, organelles, added reagent (binding), and/or complexes thereof, among others. The detected characteristics also may include cellular characteristics, such as any suitable cellular genotype or phenotype, including morphology, growth, apoptosis, necrosis, lysis, alive/dead, position in the cell cycle, activity of a signaling pathway, differentiation, transcriptional activity, substrate attachment, cell-cell interaction, translational activity, replication activity, transformation, heat shock response, motility, spreading, membrane integrity, and/or neurite outgrowth, among others.

VI. OUTPUT MECHANISMS

Microfluidic systems may include one or more output mechanisms that interface with the microfluidic network(s). An output mechanism generally comprises any suitable mechanism for outputting material(s) (e.g., fluid, particles, and/or reagents) from a microfluidic system, or portions thereof, including selective and/or bulk mechanisms. The output mechanism may direct outputted material to any suitable location, such as an internal and/or external sink. A sink generally comprises any receptacle or other site for receiving outputted materials, for disposal (e.g., a waste site) or for further study or manipulation (e.g., a collection site). The outputting of materials from the microfluidics system may be facilitated and/or regulated using any suitable facilitating mechanism, such as sources of internal pressure and/or external vacuum. The output mechanism may include a selection mechanism, such as a filter, that selects outputted materials based on some criterion, such as whether the material is a particle or a fluid.

VII. DESCRIPTION OF AN ON-DEMAND CELL DISPENSING SYSTEM

This disclosure describes microfluidic methods and systems for on-demand dispensing of particles such as those described in Section III above. The terms "particle" and "cell" are used interchangeably herein to indicate any such object.

FIG. 1 shows a schematic view of an illustrative on-demand cell dispensing system 10. In some examples, system 10 may include a microfluidic chip configured to detect particles moving in a channel and to selectively dispense one or more of the detected particles, for example, onto a substrate or into a target vessel. In some examples, the microfluidic chip may be placeable into an instrument and may be disposable following use. The microfluidic chip may be configured to engage with a manifold in the instrument to establish fluidic connections and provide a source of liquid to the chip and system.

System 10 may include a cell passage or channel 12 configured to direct a moving and/or pressurized solution 14 containing one or more particles. Channel 12, and other channels discussed herein, may include any suitable structure configured as a microfluidic pathway for conducting a fluid, and may be any suitable shape or size as described above in Section II. Solution 14 may include particles in a buffer or other liquid, and may be hydrodynamically focused, such as by using a sheath fluid.

System 10 may include a sensing region 16 configured to detect the presence of a particle of interest in channel 12 and to communicate that detection information to a controller 18. Sensing region 16 may include any suitable detector and/or sensor configured to detect the presence of a particle meeting certain selected criteria. For example, sensing region 16 may include optical, electrical, electromagnetic, and/or chemical detectors. Various detection methods may be used, independently or in combination, such as forward- or side-scatter signals, impedance measurements (e.g., Coulter counters), ferrous particles, photomultiplier tube (PMT), and/or fluorescence activated cell sorting (FACS), and/or any other suitable detection and measuring method described above in Section V.

System 10 may include one or more sensing regions 16. For example, sensing regions may be arranged in series to detect particles not previously detected and removed from channel 12 or arranged in parallel to detect particles in multiple branches of channel 12. In some examples, additional sensing regions may be included in a destination channel or other suitable location to provide verification of expected particle relocation.

Controller 18 may include any suitable electronic controller configured to receive detection information from sensing region 16 and take selected actions in response to the information received. For example, controller 18 may include a microprocessor and a digital memory configured to store instructions carried out by the microprocessor in response to certain inputs. In some examples, controller 18 may respond to an input from sensing region 16 indicating that a particle meeting predetermined criteria has been detected. Controller 18 may then initiate an output signal causing actuation of a diverter mechanism 20.

Diverter mechanism 20 may include any suitable device configured to move the detected particle from channel 12 into a dispensing channel 22, which may contain or selectively contain a pressurized dispensing fluid 24. Diverter mechanism 20 may include one or more active or passive mechanical components, motors, hydraulics, pneumatics, pressurized fluidics, vacuum generators, electrical or magnetic fields, thermal expansion and/or contraction, piezoelectric components, and the like. In some examples, diverter mechanism 20 may physically redirect a bulk of solution containing the particle. In some examples, diverter mechanism 20 may urge the particle into dispensing channel 22 through an interconnecting pathway. In some examples, diverter mechanism 20 may utilize valves or other suitable devices to control dispensing fluid 24, which may be used to confine, flush, and/or carry the particle into or through dispensing channel 22.

Undiverted particles and solution 14 may continue to a waste collection area 26, while diverted particles, solution 14, and/or dispensing fluid 24 may be directed to a dispensing area 28. Waste collection area 26 may include a collection device such as a vial or container, or may be redirected to an input of channel 12 for additional particle diversion, or elsewhere for additional processing. Cell solution 14 may be reused as appropriate.

The diverter mechanism of system 10 may divert a bulk of liquid surrounding the particle of interest into a dispensing area, for example, via a nozzle. This may facilitate a reduction in adverse effects due to manufacturing or operational tolerances on dispensing efficiency. Moreover, in this manner a dispensed cell or particle is kept in an aqueous environment, which may be critical to maintaining its health and/or structural integrity.

Dispensing area 28 may include any suitable location where a user wishes the particle or particles to be dispensed. For example, dispensing area 28 may include one or more locations on a substrate, or a target vessel. Moreover, system 10 may include multiple diverter mechanisms 20 and/or dispensing channels 22. Accordingly, system 10 may be configured as a sorting device in which cells are diverted and dispensed according to their sensed characteristics.

System 10 may be mounted on a stable frame, preventing vibration which may affect performance. In some examples, a vessel such as a micro-well plate may be placed under a dispensing nozzle, so that dispensed liquid as well as particles rests at the bottom of the plate wells. The vessel may be placed on an X-Y stage in order to control the position of the wells with respect to the dispensing nozzle. Dispensing of multiple particles into the same position may be achieved by maintaining the substrate/vessel in place. The system preferably includes mounting features, such as holes or apertures, allowing it to be easily positioned in a dedicated instrument. An assembled system may include a microfluidic chip which is sealed by means of a laminate and a manifold on which a valve is mounted. Generally, the manifold assembly is a permanent piece and the chip assembly may be either disposable or washable. The manifold may contain a valve for providing pressurized liquid to the chip on demand. In order to provide the required liquid or buffers to the chip, the manifold assembly may engage with the chip and seal by means such as o-rings, a flexible gasket, and/or surface-to-surface contact.

VIII. EXAMPLES

This section describes selected aspects and embodiments of the present disclosure related to on-demand cell dispensing devices and/or hydrodynamic focusing mechanisms, as well as related systems and/or methods. These examples are intended for illustration only and should not limit or define the entire scope of the present disclosure. Each example may include one or more distinct inventions, and/or contextual or related information, function, and/or structure. The features disclosed in this section may be combined with each other and with features disclosed in other sections.

Example 1. Dispensing System Having a Multi-Dimensional Hydrodynamic Focusing Mechanism This example describes an on-demand cell dispensing system 200 having a hydrodynamic focusing mechanism according to aspects of the present disclosure; see FIGS. 2-11.

System 200 is an example of system 10 described above, embodied on a single layer microfluidics chip 202. System 200 includes a sheath fluid channel 204 having a sheath inlet port 206, a sample port 208, and a focusing mechanism 210 disposed at the intersection of sheath fluid channel 204 and the sample port. Sheath fluid and sample fluid combine in focusing mechanism 210, and exit the mechanism via a sheathed sample channel 212. System 200 may include a diverter mechanism 214, configured to divert particles of interest from channel 212 toward a dispensing nozzle 216.

In operation, chip 202 may be oriented as shown (i.e., on edge), with the dispensing nozzle pointed in a downward direction and the focusing mechanism oriented vertically with respect to the earth. However, unless specifically stated otherwise, directions and dimensions will be referred to herein relative to the channels and the flows within those channels. Accordingly, "up" or "over" will refer to a direction generally away from a floor of the channel, the floor being the bottom of a channel formed in the chip substrate, as opposed to the ceiling of a channel (e.g., barrier formed by an applied film layer). Likewise, "lateral" or "horizontal" will refer to a direction generally toward or away from the walls of a channel, and "axial," "flow-wise," or "upstream/downstream" will refer to directions generally parallel to or in line with fluid flow through a channel or other feature. Corresponding terms should be interpreted in similar fashion. In some descriptions, directions or dimensions may additionally or alternatively be referred to in terms of X, Y, and Z, which are mutually orthogonal directions as shown in the associated drawings.

Focusing mechanism 210 may be referred to as a two-dimensional (2D) or three-dimensional (3D) hydrodynamic focusing mechanism or chamber. Focusing mechanism 210 may include any suitable structure configured to hydrodynamically focus or direct a fluid containing one or more particles in two or three dimensions without the substantial formation of bubbles in the fluid. Focusing mechanism 210 may hydrodynamically focus such a sample fluid in the up-down direction (i.e., heightwise), as well as the side-to-side (i.e., lateral) direction, resulting in 2D focusing. Flow is proceeding in these examples down a long axis of one or more channels. Accordingly, hydrodynamic focusing may be referred to as radial focusing of the sample stream, in that it involves focusing of the sample fluid in directions transverse to the axis of flow.

In some examples, particles may also be deliberately spaced from each other in a flow-wise direction (i.e., axially) by the focusing mechanism (e.g., by accelerating an outlet flow as compared to an inlet flow), resulting in a third dimension of focusing (i.e., spaced axial particle flow). In the example shown, focusing mechanism 210 includes an inlet 218, a shaped chamber 220, and an outlet 222.

Chamber 220 may form a laterally expanded portion of channel 204, and may include any suitable structure configured to facilitate spatial separation and combination of two fluids as described below. Generally speaking, chamber 220 is shaped in a flow-wise direction such that the chamber first widens and then narrows. In some examples, chamber 220 may have a generally quadrilateral shape, such as a simple convex quadrilateral, with a corner of the quadrilateral being disposed at inlet portion 218 and an opposing corner being disposed at outlet portion 222. Additionally, a floor of chamber 220 may include a spigot or island portion 224, generally centered within the chamber and raised relative to the channel floor. Sample port 208 is formed in island portion 224, and disposed such that the sample port enters the chamber orthogonally, i.e., up through the island portion.

In the example shown, chamber 220 and island 224 are generally concentric and each has the shape of a diamond, also referred to more specifically as a convex kite. Here, a kite is defined as a quadrilateral having two pairs of equal-length sides, each pair of equal length sides sharing a corner or angle (i.e., the two sides of the pair are adjacent to each other). In the illustrative island 224 shown in FIGS. 5 and 6, a shorter pair of sides 226 is oriented downstream of a longer pair 228.

Island 224 may be shaped similar to chamber 220, but having smaller lateral and vertical dimensions, thereby leaving a gap at each lateral side to form side paths 230 and 232, as well as above the island to form an overhead path 234.

In this example, a sheath fluid 236 passes into chamber 220 via inlet 218, which may be larger in size than outlet 222. Upon reaching island 224, the sheath fluid is forced to pass both around and over the island, forming portions of the stream through paths 230 and 232 (circumventing the island), as well as 234 (passing over the island). A sample fluid 238 containing one or more particles may be introduced at sample port 208. Sample port 208 is downstream of the formation of separate flow pathways. Accordingly, upon entry into the chamber, sample fluid 238 is focused laterally by sheath fluid 236 passing through paths 230 and 232, and above by sheath fluid 236 passing through path 234. Island 224 forms a barrier below sample fluid 238 as it is carried downstream by the sheath fluid flow.

As sheath fluid 236 and sample 238 continue to flow through chamber 220, side paths 230 and 232 (and the streams of sheath fluid 236 flowing through them) converge as island 224 terminates. Sheath fluid 236 continues flowing along the floor of outlet portion 222 into channel 212, while sample 238 flows substantially horizontally off the top surface of the island. Sheath fluid 236, already constraining the sample laterally and above, thereby further constrains or focuses sample 238 from below. At this point, sample 238 has been focused in both a lateral, side-to-side dimension and a vertical, up-and-down dimension. In other words, the sample has been hydrodynamically focused in both the Y and Z dimensions. Accordingly, this type of hydrodynamic focusing may be referred to as two-dimensional, or 2D, focusing.

The height of the island, i.e., the distance between the top of island portion 224 and the floor of side paths 230 and 232, may at least in part determine the position of core sample flow along the height of channel 212. Suitable heights may be determined by empirical and/or numerical analysis, for example, using finite element software such as COMSOL Multiphysics™ software. Suitable heights may be defined in terms of channel dimensions and may include no more than (e.g., less than) about half the height of the channel, between about one-sixth and about one-half the height of the channel, between about three-twelfths and about five-twelfths of the height of the channel, and/or about one-third the height of the channel, among others. Suitable heights may also be defined in terms of particle dimensions and may include at least about one particle diameter, at least about one-and-a-half particle diameters, and/or at least about two particle diameters, among others. Suitable heights also may be defined in terms of sample port dimensions and may be less than a diameter of the sample port, about the same as a diameter of the sample port, or greater than a diameter of the sample port. Yet other measures and dimensions of heights may be appropriate, depending on other dimensions and components, particle type, and so on.

The shape and position of island 224 also may at least in part determine the position of core sample fluid. The island may be at least substantially symmetric in shape and position with respect to the sample port (and/or focusing chamber), at least transverse to the general direction of fluid flow, so that approximately equal volumes of fluid travel along each of side paths 230 and 232. Such symmetry may bias particles toward the center of channel 212.

The island may be at least substantially symmetrical in shape and position in the direction of fluid flow. However, in some embodiments, the island may have a kite shape, as discussed above. In other words, the island may taper more quickly upstream or downstream of the sample port. For example, in the embodiment shown, the island tapers more quickly downstream of the sample port, such that the island is relatively longer upstream from the sample port and relatively shorter downstream from the sample port. This length may be at least several times the height of the channel and/or at least several times a diameter of the particles, upstream and/or downstream from the sample port. The sides of the island may taper more slowly than the walls of the focusing chamber, at about the same rate as the walls of the focusing chamber, or faster than the walls of the focusing channel, such that the dimensions of the side paths may increase, decrease, or stay the same.

System 200 may include one or more alignment features, such as aperture 240 formed in chip 202, for aligning the system with other equipment. System 200 may include channels of varying dimensions. Individual channels may have different dimensions (e.g., width) at different locations, to facilitate equalization of hydraulic resistance between various portions of the system. For example, an individual channel may change depth using a ramping feature, as shown at 242 and 244 in the drawings.

System 200 may include a diversion fluid channel 246, interchangeably referred to as an actuation fluid channel, having an inlet port 248, and a diverter mechanism 214 at the intersection of channel 246 and channel 212. Sheathed sample channel 212 terminates in a collection port 252.

Diverter mechanism 214 may include any suitable structures and/or arrangement of channels configured to redirect a particle of interest from channel 212 to a dispensing channel 254 rather than allowing the particle to continue to collection port 252. In the example depicted in FIGS. 9 and 10, diverter mechanism 214 includes a forking or branching of diversion fluid channel 246. Diversion fluid channel 246 splits to form two smaller channels, branches 256 and 258, also referred to as path A and path B, before intersecting with sheathed sample channel 212.

Figure 9:
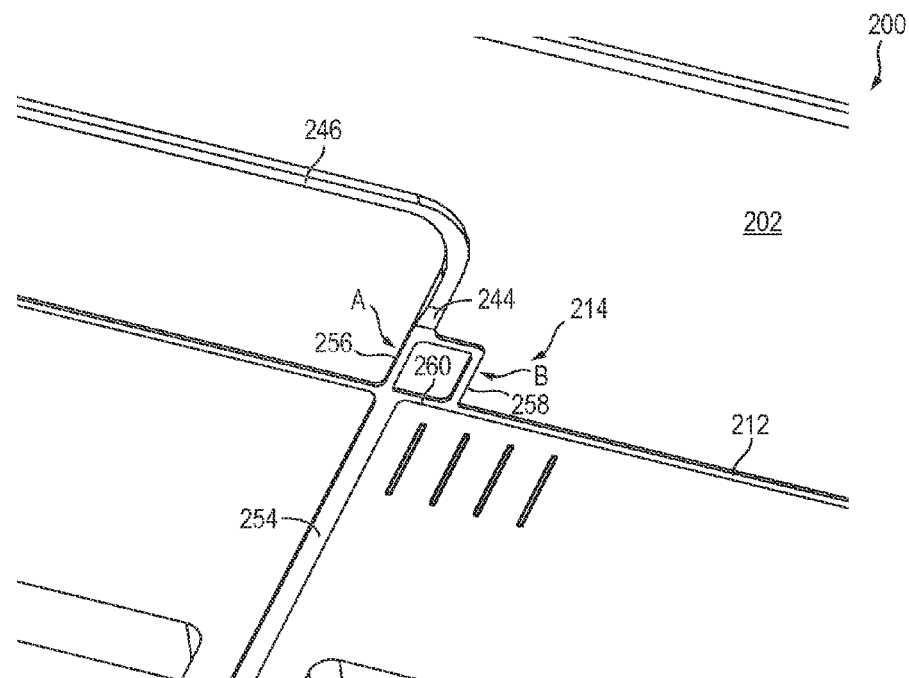
FIG. 9 is a partial isometric view of the chip of FIG. 2, showing an illustrative dispensing mechanism in accordance with aspects of the present disclosure.
Figure 10:
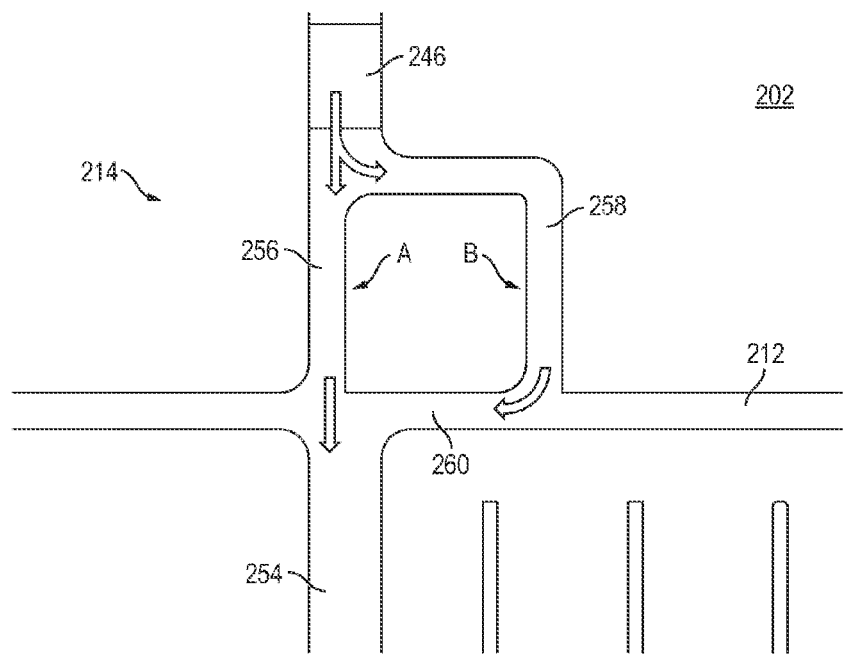
FIG. 10 is a plan view of the dispensing mechanism of FIG. 9.
Figure 11:
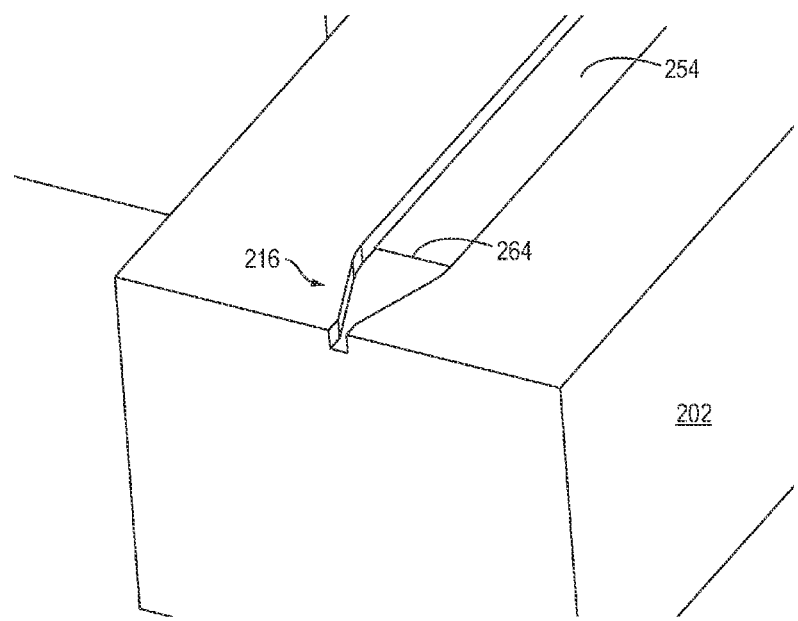
FIG. 11 is a partial isometric view of the chip of FIG. 2, showing an illustrative dispensing nozzle in accordance with aspects of the present disclosure.

Branches 256 and 258 may include any suitable arrangement of channels in which path A is substantially shorter than path B, and in which path B terminates at an intersection with channel 212 upstream and spaced from the intersection of path A with channel 212. In this example, as shown in FIGS. 9 and 10, branch 256 is configured as a straight path continuing in the direction of the long axis of channel 246. Branch 258 splits from channel 246 at a ninety-degree (or similar) angle, turning again after a certain distance to run parallel to branch 256 and intersect with channel 212. Accordingly, branch 258 forms a significantly longer path than branch 256.

Because the branches and paths are of unequal length and substantially identical cross-section, fluid travelling down path A will reach an intersection with channel 212 before fluid travelling down path B. Accordingly, flow in sample channel 212 will be effectively blocked by the incoming flow from branch 256 (which will continue through the intersection and on through dispensing channel 254). This action blocks the particle from proceeding to collection.

Diversion fluid travelling down the second branch then intersects upstream of the blocked particle and flushes (e.g., carries or pushes) it through dispensing channel 254, along with a surrounding portion of the sample-containing carrier fluid. In this embodiment, one or more valves or other control mechanisms for fluid(s) may be located off-chip. In other words, diverter mechanism 214 may include no moving parts, and may be manufactured using conventional injection molding methods.

Diversion fluid channel 246, branch 256, and dispensing channel 254 may all be substantially aligned directionally at a right angle to sheathed sample channel 212. In other examples, various other angles and arrangements may be suitable. In this example, dispensing channel 254 terminates in nozzle portion 216, which is configured for dispensing a diverted particle.

Operation of system 200 will now be described in more detail. Pressurized sheath fluid is introduced at port 206 and flows through sheath fluid channel 204 toward focusing mechanism 210. A particle-containing sample fluid is introduced at sample port 208, passing into focusing chamber 220. The sample is hydrodynamically and multi-dimensionally focused at the focusing chamber, as described above regarding chamber 220, and the sheathed sample continues down sheathed sample channel 212. Absent further system activity, the sheathed sample passes through diverter mechanism 214 and exits the system via collection port 252.

Sample flow may be monitored for particles of interest, continuously or intermittently, at a sensing region 262. The 2D/3D focusing described above facilitates detection and improves the accuracy of dispensing. Once the sample particles are focused and spaced properly, any suitable detection mechanism such as imaging or forward scatter can be used to accurately distinguish individual particles and determine a proper time delay for dispensing actuation.

In this example, dispensing (also referred to as dispensing actuation and/or diversion), includes the introduction of a pressurized actuation fluid at inlet port 216. The flow of actuation fluid (also referred to as diverter fluid or diversion fluid) may be controlled by a valve. In some examples, the valve may be located off-chip, such as at the source of diverter fluid. Once a particle of interest has been identified in the sensing region, a controller will pressurize diversion fluid channel 246, timing the release of fluid to ensure the particle is trapped and dispensed as explained further below.

As pressurized actuation fluid travels toward channel 212, it splits to pass through branches 256 and 258. Because path A is shorter than path B, the liquid traveling through branch 256 arrives at the intersection with channel 212 first, and continues to flow through the intersection into the dispensing channel. This action blocks the particle of interest and surrounding fluid from passing on toward collection port 252. After a brief delay caused by the greater length of path B, pressurized liquid arrives at the intersection of branch 258 and channel 212 upstream of the trapped particle. Flow continues, pushing the particle toward and into the dispensing channel as the pressurized path A and path B actuation streams merge.

The volume of channel 212 defined between the channel's intersections with branches 256 and 258 may be referred to as a dispensing region 260. Trapping and dispensing a volume of sheathed sample fluid in the manner described allows system 200 to dispense any particle in the dispensing region, thereby greatly increasing the reliability of the system by reducing the effects of manufacturing tolerances, variations in flow rate, viscosity, etc.

Relative pressures of the liquids in the system are maintained such that pressure in the dispensing channel is lower than surrounding regions, helping to ensure that particles are directed into the dispensing channel when actuation fluid is released. After a suitable time or upon confirmation that the particle of interest has been successfully diverted, the controller cuts off flow of the pressurized actuation fluid in preparation for a subsequent diversion event. Flow of sheathed sample fluid is allowed to pass through diverter mechanism 214 to collection port 252.

Nozzle 216 is formed in the distal end of dispensing channel 254 by tapering or narrowing the channel. This narrowing is configured to eliminate dead zones and to allow capillary action to resist leakage via the nozzle section during normal operation. A step 264 may be present in the floor of channel 254 near the proximal end of nozzle 216, changing the depth of the channel slightly. This change may function to provide further leakage prevention and/or alter a hydraulic characteristic of the nozzle. A hydrophobic material may be added to nozzle 216, such as by applying a coating, to further enhance this resistance. This embodiment does not include an outlet valve, instead relying on the capillary action of the nozzle. When a diversion occurs, the pressure from the actuating fluid released into the dispensing channel will overcome the capillary action and any hydrophobic coating, and dispense the particle through nozzle 216. Accordingly, dispensing may occur only at pressures above a certain threshold, for example, above about 1 psi. This results in a reduction in manufacturing costs by eliminating a valve, and allows the amount of fluid dispensed with the particle to be controlled by operation of the inlet valve. The longer the actuation fluid is pressurized, such as by opening a valve, the more fluid is dispensed. Typical volume of dispensed liquid may be from about 100 to about 1000 nL.

Example 2. System

Figure 12:
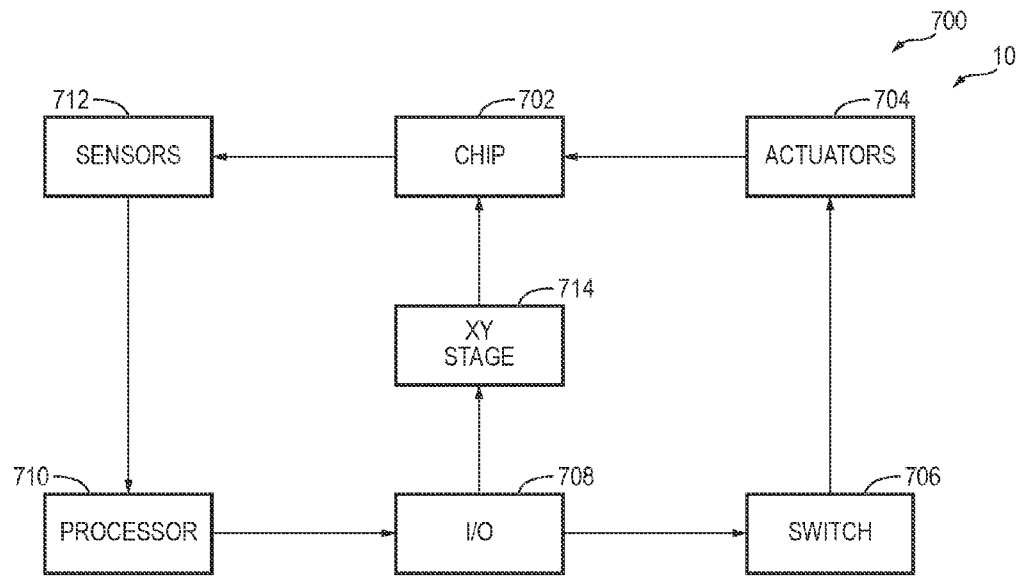
FIG. 12 is a schematic view of an embodiment of the system of FIG. 1, including a control system and substrate positioning mechanism.

This example describes an on-demand cell dispensing system 700 according to the present disclosure; see FIG. 12.

FIG. 12 is a schematic diagram showing an illustrative system 700 which is an example of system 10. System 700 includes a microfluidics chip 702 on which is located a system including the channels, focusing mechanism, and one or more diverter mechanisms described above. Chip 702 may include one or more attachment and/or reference points for facilitating assembly and alignment, such as apertures, recesses, and the like. Various devices such as valves, sliders, vacuum chambers, and other components that may be located on chip 702, or on other equipment operatively connected thereto, are caused to operate by actuators 704 such as solenoid valves. These actuators 704 are in turn activated by switches 706 controlled through an input/output (I/O) system 708 by a processor 710. Processor 710 may include a microprocessor, such as the processor of a typical personal computer or similar device, and may be in communication with a memory or storage device containing instructions for the processor to carry out. The controller described above may include the combination of processor 710 and the storage device.

Processor 710 receives input from sensors 712, such as a camera system or other detection device used in a sensing region on the chip. Chip 702 may be mounted on or associated with an X-Y stage 714 such that the chip or a substrate onto which the chip dispenses particles can be precisely located and repositioned as desired.

Example 3. Selected Embodiments

This section describes additional aspects and features of on-demand particle dispensing systems, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations. References to preceding paragraphs, such as "paragraph A" or "any of the preceding paragraphs," are to paragraphs within the same subsection of "selected embodiments."

Selected Embodiments I

1. A method of hydrodynamically focusing a fluid sample containing one or more particles, the method comprising: streaming a sheath fluid through a first microfluidic channel; passing the sheath fluid into an inline chamber having a central island projecting into the chamber, such that the sheath fluid flows around and over the island; introducing a particle-containing fluid sample through an aperture in the island, such that the fluid sample is carried along with the sheath fluid and confined radially by the sheath fluid; and passing the sheath fluid and sample into a second microfluidic channel.

2. The method of paragraph 1, further including spacing one or more particles from each other along an axis of flow.

3. The method of any one of paragraphs 1-2, wherein spacing the one or more particles includes streaming fluid in the second channel at a faster rate than fluid in the first channel.

4. The method of any one of paragraphs 1-3, wherein the island and the chamber form substantially concentric, generally quadrilateral shapes, and a portion of the sheath fluid flows around the island through an opposing pair of side paths formed between the edges of the island and the edges of the chamber.

5. The method of paragraph 4, wherein the first channel and the second channel are in fluid communication with opposite corners of the chamber.

6. The method of paragraph 5, wherein the island and the chamber have the shape of a convex kite, and a shorter pair of sides of the island meet at a corner adjacent to the second channel.

7. The method of paragraph 4, wherein the first channel, the second channel, and the chamber are formed in a common substrate, and the substrate is oriented such that the corners of the chamber lie in a plane that is vertical relative to the earth.

8. A method of hydrodynamically focusing a particle-containing sample, the method comprising: streaming a sheath fluid through a first channel; splitting the streaming sheath fluid into a plurality of substreams by forcing the sheath fluid to pass around a shaped structure inside a chamber; streaming a particle-containing sample into the chamber; radially surrounding the sample stream with the plurality of substreams of the sheath fluid; and axially flowing the radially surrounded sample into a second channel.

9. The method of paragraph 8, wherein the chamber has a generally quadrilateral-shaped perimeter.

10. The method of any one of paragraphs 8-9, wherein the shaped structure includes an island projecting into the chamber, and the island has substantially the same shape as the chamber.

11. The method of paragraph 10, wherein the island projects into the chamber by a constant distance, the distance defining a height of the island.

12. The method of paragraph 11, wherein the height of the island is approximately ⅓ the height of the chamber.

13. The method of any one of paragraphs 8-9, wherein streaming the sample into the chamber includes streaming the sample through a substantially central port formed in the shaped structure.

14. The method of any one of paragraphs 8-9, further including single-spacing particles in the sample stream in the second channel.

15. The method of paragraph 14, wherein single-spacing includes accelerating the sample stream flow.

16. An on-demand particle dispensing apparatus comprising: a microfluidic chip including a network of channels; a hydrodynamic focusing mechanism formed inline with a first channel of the network of channels, the hydrodynamic focusing mechanism including a shaped chamber, a raised island centrally disposed in the chamber forming flow pathways over the island and along the chamber perimeter, and a sample fluid port formed in the island; a diverter mechanism including a branched second channel that intersects the first channel downstream of the focusing mechanism; and a dispensing channel intersecting the first channel at the diverter mechanism and terminating in a dispensing nozzle; wherein the diverter mechanism is configured to selectively divert a bulk of fluid into the dispensing channel by flowing a diversion fluid through the branched second channel, through the first channel, and into the dispensing channel.

17. The apparatus of paragraph 16, wherein the shaped chamber and the raised island each has the shape of a quadrilateral having two corners in line with the first channel.

18. The apparatus of any one of paragraphs 16-17, wherein the second channel includes a first branch and a second branch having a substantially longer path length than the first branch.

19. The apparatus of any one of paragraphs 16-18, wherein the sample fluid port is formed in a central portion of the island.

20. The apparatus of any one of paragraphs 16-19, wherein a height of the island is less than approximately one-half of a height of the chamber.

21. The system of paragraph 19, where the sample port can have either a pre-attached tube which can be inserted directly into a sample source or an on-board reservoir to avoid cross contamination.

22. The system of any one of paragraphs 16-21, where the nozzle comprises a narrow section at a distal end, the nozzle being configured to provide sufficient capillary pressure to prevent leakage.

23. The system of paragraph 22, where the nozzle further comprises a widened section to allow for flow of liquid with minimal resistance.

24. The system of paragraphs 22 or 23, wherein the nozzle comprises a hydrophobic coating to increase capillary pressure.

Selected Embodiments II

This subsection presents selected embodiments of the present disclosure, described as a first series of numbered paragraphs.

A. A method of hydrodynamically focusing a fluid sample containing a particle, the method comprising (1) streaming a sheath fluid through a first channel; (2) passing the sheath fluid through an inline chamber having a central raised island configured to cause the sheath fluid to pass laterally around and vertically over the island within the chamber; (3) introducing the fluid sample through an aperture in the raised island such that the fluid sample is carried along with the sheath fluid and confined laterally and vertically by the sheath fluid; and (4) passing the sheath fluid and sample into a second channel.

B. A method of hydrodynamically focusing a particle-containing sample, the method comprising (1) separating a sheath fluid into a plurality of streams by passing the sheath fluid through a shaped chamber having a raised central island; (2) passing the separated streams of sheath fluid around a sample both horizontally and vertically; and (3) passing the combined sample and sheath fluid into a channel.

C. A method of hydrodynamically focusing a particle-containing sample, the method comprising (1) splitting a pressurized sheath fluid into a plurality of streams by forcing it to pass over a shaped structure inside a chamber; (2) introducing a sample into the chamber; (3) surrounding the sample in two dimensions with the streams of the sheath fluid; and (4) passing the surrounded sample into an outlet channel.

D. A method of hydrodynamically focusing a particle-containing sample, the method comprising (1) directing a sheath fluid over and around a central raised island in a shaped chamber; and (2) within the chamber, combining the sheath fluid traveling in a first direction with a pressurized sample traveling in a second direction orthogonal to the first direction.

1. The method of any of paragraphs A to D, wherein the chamber is diamond shaped or kite shaped.

2. The method of any of the preceding paragraphs, wherein the raised island is substantially the same shape as the chamber.

3. The method of any of the preceding paragraphs, wherein a height of the raised island is constant.

4. The method of any of the preceding paragraphs, wherein a height of the raised island is approximately ⅓ the height of the chamber.

5. The method of any of the preceding paragraphs, wherein the chamber has a height substantially the same as a channel.

6. The method of any of the preceding paragraphs, wherein the sample is introduced into substantially the center of the chamber.

7. The method of any of the preceding paragraphs, wherein the sheath fluid is split horizontally into two lateral streams, and further including recombining a portion of the two lateral streams to form a stream below the sample.

8. The method of any of the preceding paragraphs, wherein hydrodynamically focusing the sample includes forcing particles to be spaced singly in an outlet channel.

9. The method of any of the preceding paragraphs, further including diverting and dispensing a particle and surrounding sample fluid through an outlet channel.

10. The method of any of the preceding paragraphs, further including sorting particles in the sample based on at least one selected criterion by selectively diverting and dispensing the particles into one or more outlet channels.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of hydrodynamically focusing a fluid sample containing one or more particles, the method comprising:
   streaming a sheath fluid through a first microfluidic channel;
   passing the sheath fluid into an inline chamber having a central island projecting into the chamber, wherein the island has smaller lateral and vertical dimensions than the chamber, thereby leaving a gap at each lateral side of the island to form side paths, and a gap above a top surface of the island to form an overhead path, such that the sheath fluid flows around the island on the side paths and over the island on the overhead path;
   introducing a particle-containing fluid sample into the chamber through an aperture in the island, such that the fluid sample is carried downstream along the top surface of the island with the sheath fluid and confined radially by the sheath fluid; and
   passing the sheath fluid and fluid sample into a second microfluidic channel.

2. The method of claim 1, further including spacing one or more particles from each other along an axis of flow.

3. The method of claim 2, wherein spacing the one or more particles includes streaming fluid in the second channel at a faster rate than fluid in the first channel.

4. The method of claim 1, wherein the island and the chamber form substantially concentric, generally quadrilateral shapes.

5. The method of claim 4, wherein the first channel and the second channel are in fluid communication with opposite corners of the chamber.

6. The method of claim 5, wherein the island and the chamber have the shape of a convex kite, and a shorter pair of sides of the island meet at a corner adjacent to the second channel.

7. The method of claim 4, wherein the first channel, the second channel, and the chamber are formed in a common substrate, and the substrate is oriented such that the corners of the chamber lie in a plane that is vertical relative to the earth.

8. The method of claim 1,
   wherein the first and second channels, the chamber, the island, and the side paths are defined by a planar chip.

9. The method of claim 1, wherein the chamber has a generally quadrilateral-shaped perimeter.

10. The method of claim 1, wherein the island has substantially the same shape as the chamber.

11. The method of claim 1, wherein the island projects into the chamber by a constant distance, the distance defining a height of the island.

12. The method of claim 11, wherein the height of the island is approximately ⅓ the height of the chamber.

13. The method of claim 1, wherein introducing includes streaming the sample through a substantially central port formed in the island.

14. The method of claim 1, further including single-spacing particles of the sample in the second channel.

15. The method of claim 14, wherein single-spacing includes accelerating flow of the sample.

16. The method of claim 1, wherein the side paths are created by furrows, and wherein each furrow shares a wall with a lateral side of the island.

* * * * *